(12) United States Patent
Kibblewhite

(10) Patent No.: US 7,650,792 B2
(45) Date of Patent: Jan. 26, 2010

(54) LOAD INDICATING MEMBER WITH IDENTIFYING ELEMENT

(75) Inventor: Ian E. Kibblewhite, Wayne, PA (US)

(73) Assignee: Innovation Plus, LLC, King of Prussia, PA (US)

( * ) Notice: Subject to any disclaimer, the term of this patent is extended or adjusted under 35 U.S.C. 154(b) by 0 days.

(21) Appl. No.: 12/287,760

(22) Filed: Oct. 14, 2008

(65) Prior Publication Data

US 2009/0038401 A1 Feb. 12, 2009

Related U.S. Application Data

(60) Division of application No. 11/344,029, filed on Jan. 31, 2006, now Pat. No. 7,441,462, which is a continuation-in-part of application No. 10/470,372, filed as application No. PCT/US02/03920 on Jan. 28, 2002, now Pat. No. 6,990,866.

(60) Provisional application No. 60/264,877, filed on Jan. 29, 2001.

(51) Int. Cl.
*F16B 31/02* (2006.01)

(52) U.S. Cl. .......................................... 73/761; 73/760

(58) Field of Classification Search ............ 73/760–761
See application file for complete search history.

(56) References Cited

U.S. PATENT DOCUMENTS

| | | |
|---|---|---|
| 1,909,476 A | 5/1933 | Trotter |
| 3,181,672 A | 5/1965 | Swanson |
| 3,774,479 A | 11/1973 | Lesner |
| 3,969,810 A | 7/1976 | Pagano |
| 3,969,960 A | 7/1976 | Pagano |
| 4,006,784 A | 2/1977 | Dudek |
| 4,008,772 A | 2/1977 | Boys |
| 4,043,222 A | 8/1977 | Dudek |
| 4,074,772 A | 2/1978 | Jonsson |
| 4,104,778 A | 8/1978 | Vliet |
| 4,281,538 A | 8/1981 | Dudek |
| 4,281,987 A | 8/1981 | Kleesattel |

(Continued)

FOREIGN PATENT DOCUMENTS

DE 33 27 964 2/1985

(Continued)

OTHER PUBLICATIONS

R. Adams, "Bar Code 1, 2-Dimensional Bar Code Page", Adams Communications, Apr. 12, 1999 (http://web.archive.org/web/20000229163608/http://www.adams1.com/pub/russadam/stack.html).

(Continued)

*Primary Examiner*—Max Noori
(74) *Attorney, Agent, or Firm*—Gary M. Cohen

(57) ABSTRACT

A load indicating member is provided with an identifying element which can be accessed and used to determine ultrasonic measurement parameters specific to the load indicating member to provide more precise and more reliable load measurements by compensating for differences resulting from manufacturing variations in individual load indicating members. The parameters specific to the load indicating member can be stored in coding applied to the load indicating member or in a database that can be accessed remotely, for example, using the Internet.

4 Claims, 2 Drawing Sheets

U.S. PATENT DOCUMENTS

| | | | |
|---|---|---|---|
| 4,294,122 A | 10/1981 | Couchman | |
| 4,316,512 A | 2/1982 | Kibblewhite et al. | |
| 4,333,351 A | 6/1982 | Bickford | |
| 4,344,138 A | 8/1982 | Frasier | |
| 4,471,657 A | 9/1984 | Voris et al. | |
| 4,602,511 A | 7/1986 | Holt | |
| 4,846,001 A | 7/1989 | Kibblewhite | |
| 4,899,591 A | 2/1990 | Kibblewhite | |
| 4,977,898 A | 12/1990 | Schwarzschild et al. | |
| 5,018,988 A | 5/1991 | Kibblewhite et al. | |
| 5,029,480 A | 7/1991 | Kibblewhite | |
| 5,042,015 A | 8/1991 | Stringer | |
| 5,092,175 A | 3/1992 | Winckler et al. | |
| 5,131,276 A | 7/1992 | Kibblewhite | |
| 5,165,831 A | 11/1992 | Yager et al. | |
| 5,170,277 A | 12/1992 | Bard et al. | |
| 5,211,061 A | 5/1993 | Goodwin | |
| 5,216,622 A | 6/1993 | Kibblewhite et al. | |
| 5,220,839 A | 6/1993 | Kibblewhite | |
| 5,242,253 A | 9/1993 | Fulmer | |
| 5,303,585 A | 4/1994 | Lichte | |
| 5,343,785 A | 9/1994 | Holt et al. | |
| 5,437,525 A | 8/1995 | Bras | |
| 5,726,349 A | 3/1998 | Palmertree et al. | |
| 5,807,048 A | 9/1998 | d'Agraives et al. | |
| 5,970,798 A | 10/1999 | Gleman et al. | |
| 6,009,380 A | 12/1999 | Vecchio et al. | |
| 6,053,906 A | 4/2000 | Honda et al. | |
| 6,078,874 A | 6/2000 | Piety et al. | |
| 6,142,023 A | 11/2000 | Cole et al. | |
| 6,186,010 B1 | 2/2001 | Eguchi et al. | |
| 6,239,737 B1 | 5/2001 | Black | |
| 6,268,796 B1 | 7/2001 | Gnadinger et al. | |
| 6,338,716 B1 | 1/2002 | Hossack et al. | |
| 6,340,868 B1 | 1/2002 | Lys et al. | |
| 6,341,271 B1 | 1/2002 | Salvo et al. | |
| 6,350,245 B1 * | 2/2002 | Cimino | 601/2 |
| 6,502,463 B1 | 1/2003 | Clark et al. | |
| 6,598,900 B2 | 7/2003 | Stanley et al. | |
| 6,633,821 B2 | 10/2003 | Jackson et al. | |
| 6,671,185 B2 | 12/2003 | Duval | |
| 6,712,570 B2 | 3/2004 | Kersten | |
| 6,726,960 B1 | 4/2004 | Sanduja et al. | |
| 6,843,628 B1 | 1/2005 | Hoffmeister et al. | |
| 6,907,944 B2 * | 6/2005 | Sale et al. | 175/57 |
| 6,990,866 B2 | 1/2006 | Kibblewhite | |
| 7,441,462 B2 | 10/2008 | Kibblewhite | |
| 7,467,556 B2 | 12/2008 | Kibblewhite et al. | |
| 2001/0014262 A1 | 8/2001 | Friederich et al. | |
| 2002/0044063 A1 | 4/2002 | Blagin et al. | |
| 2003/0095847 A1 | 5/2003 | Cheal | |
| 2004/0045729 A1 | 3/2004 | Lehnert et al. | |
| 2004/0050567 A1 | 3/2004 | Tambini | |
| 2004/0065154 A1 * | 4/2004 | Kibblewhite | 73/761 |
| 2006/0004290 A1 | 1/2006 | Smith et al. | |
| 2006/0123917 A1 * | 6/2006 | Kibblewhite | 73/761 |

FOREIGN PATENT DOCUMENTS

| | | |
|---|---|---|
| DE | 199 17 222 | 11/2000 |
| EP | 0 535 919 | 4/1993 |
| EP | 0 541 476 | 5/1993 |
| JP | 04-166732 A | 6/1992 |
| JP | 10-086074 | 4/1998 |
| JP | 02-002239939 A | 8/2002 |
| WO | WO 00/63565 | 10/2000 |
| WO | WO 02/061292 | 8/2002 |
| WO | WO 2004/027271 | 4/2004 |
| WO | WO 2007/089760 | 8/2007 |
| WO | WO 2007/117575 | 10/2007 |
| WO | WO 2007/139834 | 12/2007 |

OTHER PUBLICATIONS

"Insuring Your Products' Future Through Chemical Grafting", Polymer Research Corporation of America, Brooklyn, NY.

"TAPTITE 2000® Thread Rolling Fasteners" Catalog, REMINC Research Engineering & Manufacturing Inc., Middletown, Rhode Island (2001).

* cited by examiner

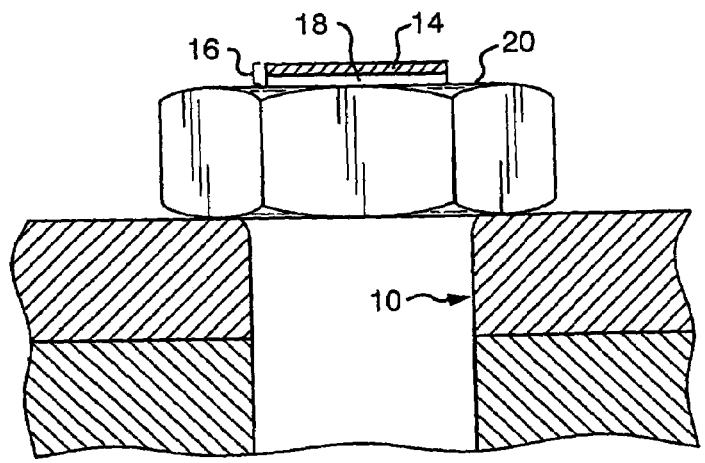
FIG. 2
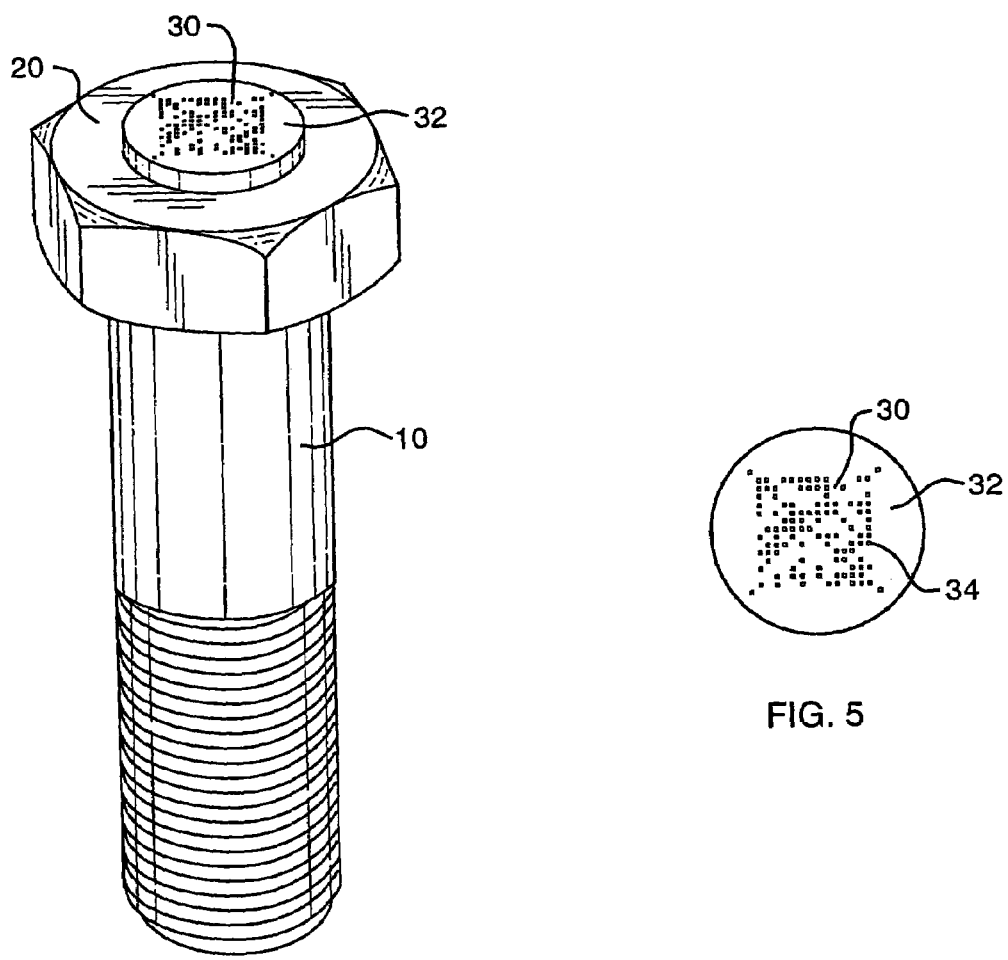
FIG. 4
FIG. 5

LOAD INDICATING MEMBER WITH IDENTIFYING ELEMENT

CROSS-REFERENCE TO RELATED APPLICATIONS

This application is a divisional of U.S. patent application Ser. No. 11/344,029, filed Jan. 31, 2006, now U.S. Pat. No. 7,441,462 which is in turn a continuation-in-part of U.S. patent application Ser. No. 10/470,372, which has an assigned filing date of Jul. 25, 2003, which was the National Stage of International Application No. PCT/US02/03920, filed Jan. 28, 2002, which claims the benefit of U.S. Provisional Application No. 60/264,877, filed Jan. 29, 2001, and which has since issued as U.S. Pat. No. 6,990,866, on Jan. 31, 2006.

BACKGROUND OF THE INVENTION

This invention relates to load indicating members and, more particularly, to load indicating members, such as fasteners, having ultrasonic transducers.

In many operations, it is desirable to determine the amount of longitudinal load experienced by a longitudinally stressed member. This information is particularly useful when the longitudinally stressed member is a fastener since the measurement of longitudinal load provides a verification of the existence of a proper joint.

Ultrasonic load measurement is a precise measurement technique for determining load in bolted joints. Pulse-echo techniques with removable ultrasonic transducers have been used in laboratories and for quality control for over thirty years. Historically, however, the practical difficulties in achieving reliable acoustic coupling and in incorporating transducers in tool drives have prevented this technique from becoming a general assembly tightening strategy.

The above coupling difficulties were overcome with permanently attached transducers. U.S. Pat. No. 4,846,001 (issued to Kibblewhite) teaches the use of a thin piezoelectric polymer film which is permanently, mechanically, and acoustically coupled to an end surface of a member and used to determine the length, tensile load, stress or other tensile load-dependent characteristic of the member by ultrasonic techniques. Although the invention represented a significant advance over the prior state of the art in terms of performance, ease of manufacture, and manufacturing cost, there are disadvantages with a transducer of this construction. These disadvantages relate to environmental performance, in particular the maximum temperature limitations of the polymer material which restricts its application, and the possibility of the transducer, fixed to the fastener with adhesive, coming loose and causing an obstruction in, or damage to, a critical assembly.

U.S. Pat. No. 5,131,276, issued to Kibblewhite and assigned to Ultrafast, Inc., teaches a load-indicating member having an ultrasonic transducer, including an acousto-electric film, grown directly on the fastener surface (i.e., a piezoelectric thin-film). By growing the acousto-electric film directly on the fastener, the film is mechanically, electrically, and acoustically interconnected to the surface. Permanent ultrasonic transducers not only allow the precise pulse-echo load measurement technique to be used in production assembly but also significantly improve accuracies by eliminating errors that result from axial and radial movement of the removable transducer relative to the bolt and from variations in the coupling media.

All the above-mentioned ultrasonic methods of determining load in a load indicating member require a zero-load measurement in addition to the measurement taken under the desired loaded condition in order to determine the absolute load in the member. Furthermore, all use a direct or indirect measurement of the out-and-return time-of-flight of a longitudinal ultrasonic wave. Holt, U.S. Pat. No. 4,602,511, teaches of a method which uses the times-of-flight of both longitudinal and transverse waves to determine the stress in a member without taking a zero-load measurement. This is desirable in the measurement of tensile load in previously installed fasteners, for example.

The use of transverse ultrasonic waves, however, requires both a transducer capable of generating transverse waves and an acoustic coupling media capable of transmitting transverse waves into the member. Special acoustic couplants are required with temporarily attached transducers, since transverse waves cannot generally be transmitted through liquids. Although adhesives can transmit transverse ultrasonic waves, generation of transverse waves using the polymer film transducers disclosed by Kibblewhite in U.S. Pat. No. 4,846,001 has not been demonstrated. Only the permanent ultrasonic transducer technology disclosed by Kibblewhite in U.S. Pat. No. 5,131,276 has demonstrated a practical method of making load measurements in fasteners without first taking a zero-load measurement using the method based on measurements of both longitudinal and transverse waves. However, accuracies of only ±15% are typically achievable with this method due to production variations in the material and geometry of the fasteners.

The above-mentioned ultrasonic load measurement methods using longitudinal waves alone are capable of precise measurements when a zero-load measurement is made prior to tightening, with typical accuracies of ±3% documented. Because of the variation in initial lengths of fasteners manufactured using production methods, measurement of installed load at a later time is only possible with ultrasonic load measurements using longitudinal waves alone by recording the zero-load length measurement. Ultrasonic load measurement instruments have the ability to store and retrieve zero-load measurements for later inspection of load.

A means of identifying each fastener for storing and retrieving zero-load length measurements with removable transducer ultrasonic load measurement instrumentation is disclosed by Shigemi et al. in Japanese Patent Application Publication No. 10-086074. Shigemi discloses a method of applying an identifying mark, such as a bar code, on the periphery of the head of the fastener. The bar code is read by an optical bar code reader and the zero-load ultrasonic length measurement is stored in memory in a control device corresponding to the identifying mark on the fastener. When reading the fastener load at a later date, the identifying mark is first read to retrieve the zero-load length measurement. Zero-load bolt length is the only ultrasonic parameter associated with a specific bolt disclosed by Shigemi. Also, the bar code disclosed by Shigemi is used for identification purposes only and contains no encoded ultrasonic measurement information. While this invention is suitable for a single instrument at a single location, storing and retrieving a zero-load length alone is inadequate in ensuring reliable precise measurement with all fastener types, with different instruments or with different ultrasonic transducers, such as at multiple service locations, for example.

A difficulty in making reliable fastener load measurements with ultrasonic pulse-echo instrumentation arises from the uncertainty in consistently identifying the same echo cycle to which time-of-flight measurements are made. Considerable distortion of the echo waveform can occur, especially with fasteners with large length-to-diameter ratios, primarily due to fastener geometry and stress distribution variations. Vecchio et al., in U.S. Pat. No. 6,009,380, disclose a multi-frequency excitation and detection method to improve the reliability of detecting the correct echo cycle when making ultrasonic time-of-flight measurements for determining fastener load. The method stores characteristics of a typical echo waveform as a reference for a particular fastener type. However, variations in echo waveforms from fasteners of the same type can be sufficiently large to prevent this method, using a single reference for a particular fastener type, from working reliably for all fasteners. Consequently, fasteners which deviate significantly from the reference waveform characteristics are unsuitable for reliable inspection with this method and must be screened out in production.

SUMMARY OF THE INVENTION

The present invention eliminates many of the disadvantages of load indicating members of the prior art and provides additional features and advantages not previously available in load indicating members, load indicating fasteners, load indicating devices and tightening tools.

The load indicating member of the present invention has a permanent identifying element which can be read and used to determine ultrasonic measurement parameters specific to the load indicating member to provide more precise and more reliable load measurements by compensating for differences resulting from manufacturing variations in individual load indicating members.

In a preferred embodiment of the present invention, a load indicating member has an ultrasonic transducer, permanently mechanically, electrically and acoustically attached to one end of the load indicating member, such that the load indicating member functions as a first electrode. The ultrasonic transducer comprises a piezoelectric element, adjacent to the end surface of the load indicating member, and an electrically conductive layer adjacent to the piezoelectric element, functioning as a second electrode. A high-density two-dimensional optically-read bar code is permanently marked on the surface of the electrode. In this embodiment, the bar code stores not only a unique identification of the load indicating member but also all of the ultrasonic parameters, specific to that load indicating member, required to make precise, reliable load measurements.

One method of making the load indicating member of the preferred embodiment of the present invention includes the steps of providing the load indicating member with its permanently attached ultrasonic transducer, measuring the ultrasonic measurement parameters and marking a bar code, in which the ultrasonic measurement parameters are encoded, on the top electrode of the transducer.

An alternative method of making the load indicating member of the present invention includes the steps of providing the ultrasonic transducer, comprising the piezoelectric element and electrode layer on which is marked a unique identifying bar code, permanently attaching an ultrasonic transducer to the load indicating member, measuring the ultrasonic measurement parameters and storing the ultrasonic measurement parameters in a database associated with the unique identifying bar code.

A method of measuring the load in a load indicating member of the present invention includes the steps of reading the bar code with an optical reader, determining the ultrasonic measurement parameters, making pulse-echo time-of-flight ultrasonic wave measurements, and calculating the precise load.

In another embodiment of the present invention, a permanent mark is applied directly to the load indicating member, and the ultrasonic transducer is applied on top of the permanent mark in such a way that the permanent mark can be detected through the ultrasonic transducer.

In yet another embodiment of the present invention, a permanent mark is applied directly to the load indicating member, and the ultrasonic measurements are made with a removable ultrasonic transducer temporarily attached to the load indicating fastener.

The high-density bar code of the present invention can be marked either with an inkjet marking system or, preferably, using a laser marking system. In an alternative embodiment, a dot code mark is made by drilling holes through the top surface layer with a laser to form the bar code.

The present invention further includes a database of ultrasonic measurement parameters and historical loading data corresponding to each load indicating member, such database being readily interconnected with measurement instruments over a computer network, such as the Internet, and preferably in a manner transparent to the measurement equipment operator.

The present invention further includes an estimation of the load in a load indicating member which has been elongated beyond its yield point during a loading operation, based on the historical loading data for that load indicating member.

In yet another embodiment of the present invention, a high-density bar code is permanently marked on a thin, durable corrosive-resistant foil and attached to a part as a label for identification purposes.

In yet another embodiment of the present invention, the top electrode of the permanent ultrasonic transducer on the load indicating member is made of a magnetic recording material, such as a nickel cobalt alloy, for example, and the bolt identification, ultrasonic measurement parameters and/or tightening data are stored and read with magnetic recording and reading devices.

In yet another embodiment of the present invention, a non-volatile memory device is applied to the ultrasonic transducer on the load indicating member, and the bolt identification, ultrasonic measurement parameters and/or tightening data are stored and read serially through an electrical connection to an electrically conductive portion of the top exposed surface of the memory device.

In yet another embodiment of the present invention, the foregoing non-volatile memory device is a radio frequency identification (RFID) chip or tag applied to the ultrasonic transducer on the load indicating member, and the bolt identification, ultrasonic measurement parameters and/or tightening data are stored and read with RFID recording and reading devices.

In yet another embodiment of the present invention, chemical grafting is used to permanently bond the layers of film or foil to form a permanent ultrasonic transducer on a load indicating member or a permanent identifying mark on a part.

It is to be understood that both the foregoing summary description and the following detailed description are exemplary, but not restrictive, of the invention.

BRIEF DESCRIPTION OF THE DRAWINGS

In the following drawings, like reference numerals refer to like elements throughout.

FIG. 2 is a partial view of a load indicating member according to the present invention.

FIG. 4 is a perspective view of an alternative example of a load indicating member according to the present invention.

FIG. 5 is a top view of the top electrode of the load indicating member of FIG. 4.

DETAILED DESCRIPTION OF THE INVENTION

A number of measurement parameters are required to determine tensile load, stress, elongation or other measure indicative of tightness of a load indicating member, such as a bolt, rivet or rod, from ultrasonic pulse-echo time-of-flight measurements. These parameters are specific to the load indicating member, the joint in which the load indicating member is installed, the ultrasonic transducer used to transmit and receive the ultrasonic waves and the instrumentation used to make the time-of-flight measurements. These parameters are used to make reliable ultrasonic measurements and determine the relationship between the ultrasonic time-of-flight measurements and load, stress or elongation, and are influenced by, for example, the material, diameter and length of the load indicating member, the effective length on the clamped joint components, the transducer acousto-electric characteristics and instrumentation timing delays. Many of these influences are effectively constant for a specific type of load indicating member and joint, and measurement parameters affected solely by these can be predetermined for a specific joint, stored in the measurement instrumentation and selected at the time of measurement. There are, however, certain parameters that vary with each specific load indicating member due to variations in their manufacturing tolerances. These include, for example, the precise length of the bolt, acoustic properties of the material, internal residual stresses and, in the case of a permanently attached ultrasonic transducer, the acousto-electric characteristics of the transducer.

When a load indicating member, such as a fastener, is being installed from a known zero-load condition, the parameters needed to compensate for these variations can be determined and used during the loading operation. However, in order to make equally precise load measurements at a later date, for example, measuring the load in pre-installed fasteners, there needs to be a practical way to store and retrieve the parameters specific to each load indicating member. This is provided in accordance with the present invention as follows.

Figure 1:
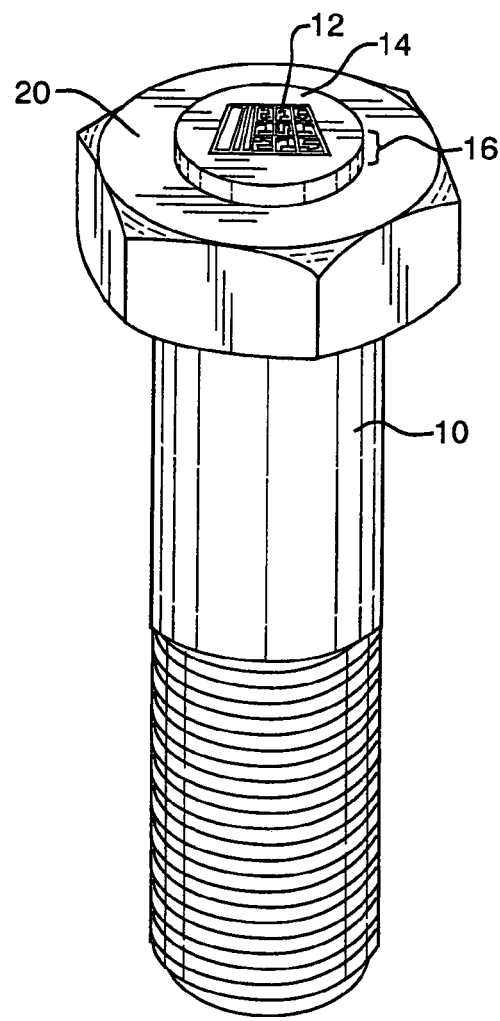
FIG. 1 is a perspective view of a load indicating member according to the present invention.
Figure 3:
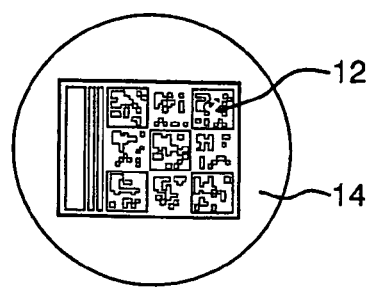
FIG. 3 is a top view of the top electrode of the load indicating member of FIG. 1.

Referring now to the drawings, and more particularly to FIGS. 1, 2 and 3 thereof, a first embodiment of a load indicating member, and more particularly, a load indicating fastener 10 is described. Load indicating fastener 10 is a fastener with a permanent piezoelectric polymer film transducer attached to one end, an example of which is disclosed in U.S. Pat. No. 4,846,001 issued to Kibblewhite, and incorporated by reference herein. The load indicating fastener of the present invention further includes a two-dimensional high-density bar code 12 on top electrode 14 of permanent ultrasonic transducer 16.

The load indicating fastener 10 is formed from a conventional bolt which has been modified to provide an indication of the tensile load, stress, elongation or other characteristic of the bolt during a tightening operation, as well as at various other times during the life of a joint. A thin piezoelectric polymer sensor 18 is permanently, mechanically and acoustically attached to end surface 20 of the bolt. In this embodiment, the piezoelectric polymer sensor 18 is a 9 micron thick, polyvinylidene fluoride copolymer film, manufactured by Measurement Specialties Inc., Valley Forge, Pa.

In this first embodiment of the present invention, top electrode 14 is a thin metallic foil, specifically approximately 50 micron thick, type 316, full-hard, dull or matte finished stainless steel, which has been treated to provide a black oxide finish. The stainless steel is available as conventional shim stock which can be specified with a rolled dull or matte finish, or alternatively, chemically treated to provide a dull or matte finish. The black oxide treatment provides an extremely thin (less than 0.5 micron), durable, corrosion resistant, electrically conductive, black coating. A durable, high-resolution bar code can be marked on this surface by removing selected areas of the coating, by conventional laser ablation techniques known in the art, to provide a high contrast mark easily read with conventional, commercially available optical readers.

In this first embodiment, the method of making the load indicating member 10 of the present invention includes the steps of providing a flat surface 20 on one end of the fastener, bonding piezoelectric film 18 to the black oxide coated stainless steel, cutting a 6 mm diameter disc of polymer/stainless steel laminate, bonding the disc to flat surface 20 such that the polymer is adjacent flat surface 20 and the stainless steel foil forms the top electrode 14 of ultrasonic transducer 16, measuring the ultrasonic measurement parameters specific to the load indicating member with ultrasonic pulse-echo instrumentation while the load indicating fastener is at zero-load, encoding measurement parameters and a unique identification into a bar code and permanently marking the bar code 12, with a laser, on the surface of the top electrode 14.

The type of bar code used in this first embodiment is preferably a high-density, two-dimensional code known as a "GoCode", which is a proprietary product of the Gocode Product Corporation, Draper, Utah. This code format provides the ability to store 34 alphanumeric characters on the 6 mm diameter stainless steel top electrode. As will be appreciated by one skilled in the art, there exist many alternative two dimensional bar code formats which could be used to store this data.

In a similar second embodiment of a load indicating member of the present invention, only a unique identification is encoded in bar code 12, and the ultrasonic measurement parameters associated with load indicating member 10 with this unique bar code are stored in a database, rather than encoded in the bar code itself. Since the data itself is not encoded within the code, unique bar codes can be marked on the stainless steel foil prior to cutting the disc and bonding it to the fastener to form the load indicating member. In this embodiment, the load measurement instruments require the data from the load measurement parameter database in order to make a load measurement in a pre-installed fastener.

An alternative method of providing a permanent durable bar code on the stainless steel of the top electrode is illustrated in FIGS. 4 and 5. A dot-type bar code 30, such as the proprietary "Snowflake" code available from Marconi Data Systems, Wood Dale, Ill., is marked on top electrode 32 with holes 34 laser drilled through the foil. Since typically less than 150 10 micron diameter holes are required for the code, their presence has an insignificant effect on the acousto-electric performance of the transducer.

In a third embodiment of the present invention, a load indicating member of the type disclosed in U.S. Pat. No. 5,131,276 (Kibblewhite), incorporated by reference herein, is provided in which a piezoelectric thin-film transducer is grown directly on one end of a fastener by a vacuum deposition method, such as magnetron sputtering. Alternatively, a load indicating member is provided in which a piezoelectric thin-film transducer is grown directly on foil by a vacuum deposition method, such as magnetron sputtering, and the transducer is then mechanically, electrically and acoustically attached to the fastener. Also provided is a surface on the top electrode, or elsewhere on the load indicating member, suitable for the marking of a bar code with the above-described marking methods, to provide the same function as those of the above-described embodiments of the present invention. Alternatively, an additional, thin color-contrasting layer could be vacuum deposited during the manufacturing operation. Parts of this layer could then be selectively removed by laser ablation, in a manner similar to that described above for the stainless steel black oxide layer, to mark the high-density bar code.

In another embodiment of the present invention, the bar code is marked on an end surface of the fastener and the ultrasonic transducer is provided on the surface with the bar code in such a manner that the bar code can be read through the transducer. In one such embodiment, the transducer layers are translucent or transparent, allowing the bar code to be read through the piezoelectric and conductive layers of the transducer. In another embodiment, the bar code is marked using an indentation technique, such as dot peening, so that the indentations are detectable, and the bar code is made readable, after application of the transducer.

In another alternative embodiment of the present invention, for use with removable ultrasonic transducers temporarily attached to a fastener, the permanent mark is applied directly to the fastener. The high-density bar code is marked on the fastener after zero-load ultrasonic measurements are made on the fastener and, as with the above-described first embodiment of the present invention, contains encoded fastener-specific ultrasonic measurement parameters. Consequently, load in the bolt can be read by different instruments and at different locations, such as service locations, without access to a database of fastener-specific ultrasonic measurement parameters. The bar code is marked on the fastener with one of the above-described methods.

It will be appreciated by one skilled in the art that there are alternative constructions of the ultrasonic transducer of the present invention. The ultrasonic transducer can be placed on a flat surface in a recess or at the bottom of a hole, for example, with internal drive fasteners. Alternative materials and thicknesses for the top electrode and for the piezoelectric element are possible, and can be selected to produce the desired durability, environmental resistance and acousto-electric performance for a particular application. Additionally, alternative piezoelectric materials, including ceramic piezoelectric materials, can be used and the piezoelectric material can be coated with thin electrically conductive layers to enhance acousto-electric performance. Alternative thicknesses of the piezoelectric element can also be used. Alternative bar code marking methods, such as inkjet marking, laser marking which heats the surface to discolor the material, and the use of laser-activated or laser-bonded coatings can be used with the present invention. Alternatively, also in the above-described embodiments, the bar codes could be marked directly on the fastener or in the vicinity of the fastener. It will be appreciated by one skilled in the art that the above-described embodiments of the present invention can be used with load indicating members using both longitudinal and transverse waves, such as those described by Kibblewhite in U.S. Pat. No. 4,846,001, and with load indicating fasteners provided with ultrasonic reflecting surfaces, such as annular grooves, as disclosed by Kibblewhite in U.S. Pat. No. 5,029,480.

For those embodiments of the present invention in which the measurement parameters are encoded directly in the bar code, the method of measuring the load in a pre-installed load indicating member includes the steps of reading the bar code with an optical reader, decoding the bar code to retrieve the ultrasonic measurement parameters, making pulse-echo time-of-flight ultrasonic wave measurements, measuring a temperature indicative of the temperature of the load indicating member, and calculating the precise load.

For those embodiments of the present invention in which the bar code is solely a unique identification of the load indicating member, the method of measuring the load in a pre-installed load indicating member includes the steps of reading the bar code with an optical reader, decoding the unique identification of the load indicating member, retrieving the ultrasonic measurement parameters associated with that unique bar code from a database, making pulse-echo time-of-flight ultrasonic wave measurements, measuring a temperature indicative of the temperature of the load indicating member, and calculating the precise load.

When measuring load in a load indicating member of the present invention during an assembly operation when a recently measured zero-load time-of-flight measurement is available, a measure of temperature is not required, since the change in temperature of the load indicating member during the assembly operation is small and typically has an insignificant effect on load measurements.

Assembly tools for use with load indicating fasteners are known in the art and are described by Kibblewhite in U.S. Pat. No. 4,846,001. Such tools are typically standard tools modified to take ultrasonic load measurements during tightening, to compare these measurements with a predetermined desired load, and to stop the tightening process by turning off the tool when the desired load is reached. If such tools are dedicated to a specific fastener type, such as on an automotive assembly line, for example, and are tightening from a zero-load condition, their associated controls can be preset with the ultrasonic measurement parameters specific to the fastener type and, therefore, do not require a bar code reading device.

A load inspection device of the present invention includes a bar code reading device, an ultrasonic pulse-echo time-of-flight measurement device, a device for inputting or measuring a temperature indicative of the temperature of the fastener, and a device for calculating load for recording or display. Preferably, the devices for measuring the bar code, the ultrasonic time-of-flight and the temperature are incorporated in a single probe to provide a simple, efficient measurement device.

In the present invention, ultrasonic measurement parameters and historical loading data corresponding to each load indicating member are uploaded to a database. The database is readily interconnected with measurement instruments over a computer network, such as the Internet, preferably in a manner which is transparent to the measurement equipment operator. The ultrasonic measurement parameters recorded during the manufacture of the load indicating member are stored in the database. During tightening of the load indicating member with an assembly tool, loading data recorded by the load measurement instrumentation is also uploaded to the database. The database, therefore, contains a complete record of the loading history of the fastener. A fastener load inspection device connected to the database can, for example, not only precisely measure the load in a fastener, but also indicate the drop in load since that fastener was installed. This information is useful in automotive and aerospace preventative maintenance operations.

It will be appreciated by one skilled in the art that the data both encoded in the bar code and stored in the database can be structured to minimize the size of the data records to be stored and transferred. For example, data common to a particular fastener type need only be stored once, and individual fastener bar codes or database records would require only a reference index to this data, such as a fastener part number, plus data specific to the individual fastener.

Ultrasonic load measurements using longitudinal waves can only measure load accurately in fasteners up until the yield point, since beyond that point the elongation is no longer elastic and permanent plastic elongation takes place. The ultrasonic load measurement method which uses both longitudinal and transverse wave times-of-flight, disclosed by Holt in U.S. Pat. No. 4,602,511 can, in theory, measure load beyond yield, but is subject to significant errors resulting from the effect of yielding on residual stresses within the fastener. In the present invention, loads beyond yield are estimated from a typical increase in time-of-flight verses yield characteristic for the specific fastener type, determined experimentally and stored in the database. Furthermore, since the complete loading history for each fastener is maintained in the database, drop in load can be determined precisely from differences between the maximum time-of-flight measurement recorded for the fastener and its then current time-of-flight.

In the above-described embodiments of the present invention, the bonding of the top electrode layer to the piezoelectric polymer 18 and the bonding of the piezoelectric polymer 18 to the top surface 20 of bolt 10 can be accomplished using an adhesive, such as an epoxy adhesive. Alternatively and preferably, this is accomplished with a process known as chemical grafting, such as that developed by the Polymer Research Corporation of America, Brooklyn, N.Y., and described in their Product Bulletin entitled "Insuring your Products' Future through Chemical Grafting". Chemical grafting uses an activator to produce a strong covalent chemical bond, rather than a physical bond. The process involves the activation, attachment and polymerization using a material-specific graft initiator-monomer system. The process can be visualized as a growth of "whiskers" onto the substrate. These whiskers attach themselves at activation sites forming polymer chains linked by covalent bonds. Chemical grafting produces such a strong bond that the materials rupture before the bond is broken. The use of chemical grafting, therefore, eliminates the disadvantage of the invention disclosed by Kibblewhite in U.S. Pat. No. 4,889,591, that the transducer can come off the load indicating member during the life of the product in which it was installed.

In yet another alternative embodiment of the present invention, a load indicating member with a permanent ultrasonic transducer uses a magnetic recording media as the material for its top electrode. Such a top electrode is manufactured from one of a number of electrically conductive magnetic materials, such as nickel or cobalt alloys and those used for aircraft flight recorders, for example. Data is recorded and read by inductive read/write heads similar to those commonly used in, for example, computer magnetic disks, audio and video recorders and magnetic strip readers. An advantage of this embodiment of the present invention is that the data, such as the ultrasonic measurement parameters, unique identification number and tightening data can be rewritten, appended to or updated by the measurement instruments.

The metal foil with the bar code marking, used for making the top electrode of some embodiments of the present invention, provides an extremely durable, corrosion and temperature resistant, permanent bar code label or tag and, therefore, this element itself can be used to uniquely identify a component or store a permanent record of critical data associated with an object in applications other than load indicating members. Such applications include the identification of aircraft parts and medical record tags, for example. When used as a label, the foil can be bonded to a component with an adhesive or by using the above-described chemical grafting.

In yet another alternative embodiment of the present invention, a non-volatile memory device is applied to a load indicating member with a permanent transducer for purposes of storing information on the ultrasonic transducer. Such memory devices can be powered, written to and read from serially through a single input/output connection and an AC coupled return through the capacitance of the ultrasonic transducer. Such devices are capable of storing data such as unique identification, ultrasonic measurement parameters, tightening and inspection data in a manner similar to that of the above-described use of magnetic media for the storage of information.

In one such embodiment, the previously described top electrode 14 is replaced with the non-volatile memory device, and portions of the top exposed surface of the memory device are made conductive by providing the surface with an electrical contact. This top conductive surface is then electrically connected to a conductive layer on the bottom of the memory device, adjacent to the active piezoelectric film layer 18 of ultrasonic transducer 16 to provide a suitable electrode for the ultrasonic transducer. The top conductive surface is also electrically connected to the non-volatile memory device for purposes of writing information to and reading information from the memory device.

In another embodiment, the foregoing non-volatile memory device is a radio frequency identification (RFID) chip or tag applied to a load indicating member with a permanent ultrasonic transducer for purposes of storing information on the ultrasonic transducer. This is accomplished with known RFID devices, such as the MetalSentinel (13.56 MHz) device available from Interactive Mobile Systems, Inc., Port Townsend, Wash., USA, which are capable of storing data such as unique identification, ultrasonic measurement parameters, and tightening and inspection data in a manner similar to that of the above-described use of magnetic recording media for the storage of information.

In this embodiment, the previously described top electrode 14 is replaced with the RFID device, and portions of the top exposed surface of the RFID device are made conductive by providing the exposed surface with an electrical contact. The top conductive surface is then electrically connected to a conductive layer on the bottom of the RFID device, adjacent to the active, piezoelectric film layer 18 of ultrasonic transducer 16 to provide a suitable electrode for the ultrasonic transducer. The piezoelectric film layer 18 of ultrasonic transducer 16 is an electrical insulator and further functions as an isolator for the antenna associated with the RFID device for purposes of RF transmission.

The size, shape and location of the conductive portions of the top exposed surface of the RFID device can vary to suit the particular RFID device which is used. For example, the conductive portions of the top exposed surface can be placed along the periphery of the RFID device, leaving the central portions of the top exposed surface open to accommodate the antenna normally associated with the RFID device. The conductive portions of the top exposed surface should preferably cover as much of the top surface of the RFID device as is possible, while leaving sufficient open space to accommodate the function of the antenna. The conductive layer on the bottom of the RFID device preferably covers the entire bottom surface, to maximize contact with piezoelectric film 18.

Various different couplings are used with RFID devices, including electromagnetic, capacitive and inductive couplings, with different coupling antennas. The antenna can be provided adjacent to non-conductive portions of the top exposed surface. Alternatively, the conductive portions of the top and bottom surfaces of the RFID device can be constructed in such a way as to function as the antenna for the transponder associated with the RFID device which is used. It will further be appreciated that non-contact inductive or capacitive couplings used for RFID transponder communication in the above described embodiments can also be used to couple the excitation signal to the ultrasonic transducer. Additionally, the RF communication frequency can be selected to correspond to a preferred ultrasonic transducer excitation frequency. This then eliminates the need for an electrically conductive top surface for electrical contact with the transducer for load measurement, allowing both the reading of information stored in the RFID device and the measurement of load to be performed even when the transducer is covered with paint or other protective coating.

It will be understood that various changes in the details, materials and arrangement of parts which have been herein described and illustrated in order to explain the nature of this invention may be made by those skilled in the art within the principle and scope of the invention as expressed in the following claims.

What is claimed is:

1. A method of measuring change in acoustic length of a load indicating member, comprising the steps of:

accessing an identifying element on the load indicating member with a reader, wherein the load indicating member is a fastener, and determining data relating to the fastener for deriving a zero-load acoustic length of the fastener and data for deriving an ultrasonic echo waveform measurement cycle used for acoustic length measurement of the fastener;

measuring the acoustic length of the fastener using an ultrasonic transducer and the derived measurement cycle; and calculating a difference between the measured acoustic length and the zero-load acoustic length and calculating the change in the acoustic length of the load indicating member from the calculated difference between the measured acoustic length and the zero-load acoustic length.

2. The method of claim 1 wherein the identifying element includes the data for deriving the zero-load acoustic length of the fastener and the data for deriving the ultrasonic echo waveform measurement cycle used for the acoustic length measurement of the fastener.

3. The method of claim 1 wherein the identifying element includes an identification of the load indicating member, and wherein the method further includes the steps of identifying the load indicating member by accessing the identifying element on the load indicating member, and retrieving from a database data relating to the load indicating member, wherein the data retrieved from the database includes the data for deriving the zero-load acoustic length of the fastener and the data for deriving the ultrasonic echo waveform measurement cycle used for the acoustic length measurement of the fastener.

4. The method of claim 1 which further includes the step of calculating load in the fastener from the calculated change in the acoustic length.

* * * * *